United States Patent

Tseng et al.

[11] Patent Number: 5,360,883
[45] Date of Patent: Nov. 1, 1994

[54] PROCESS FOR OBTAINING A POLYMERIZABLE REACTION SOLUTION

[75] Inventors: Susan Y. Tseng, Staten Island, N.Y.; Philip F. Wolf, Bridgewater, N.J.

[73] Assignee: ISP Investments Inc., Wilmington, Del.

[21] Appl. No.: 40,400

[22] Filed: Mar. 30, 1993

[51] Int. Cl.$^5$ .................................. C08F 226/10
[52] U.S. Cl. ................................. 526/264
[58] Field of Search ......................... 526/264

[56] References Cited

U.S. PATENT DOCUMENTS 4,196,276  4/1980  Schreckenberg et al. ......... 528/176
5,274,120  12/1993  Tseng et al. ..................... 548/543

Primary Examiner—Joseph L. Schofer
Assistant Examiner—Wu C. Cheng
Attorney, Agent, or Firm—Walter Katz; Marilyn J. Maue; Joshua J. Ward

[57] ABSTRACT

What is provided herein is a process for obtaining a polymerizable reaction solution which includes 5–30% by weight of a crosslinker which is the isomeric compound 1-vinyl-3(E)-ethylidene pyrrolidone and 50–80% by weight of a monomer which is vinylpyrrolidone. The polymerizable solution can be used to make crosslinked polyvinylpyrrolidone rapidly upon heating the solution at about 80°–120° C. in the absence of base.

4 Claims, No Drawings

PROCESS FOR OBTAINING A POLYMERIZABLE REACTION SOLUTION

1. Field of the Invention

This invention relates to polymerization of vinylpyrrolidone in the presence of a crosslinker to form crosslinked polyvinylpyrrolidone, and, more particularly, to a method for making a polymerizable reaction solution containing 5-30% by weight of the isomeric compound 1-vinyl-3(E)-ethylidene pyrrolidone (EVP) as crosslinker and 50-80% by weight vinylpyrrolidone as polymerizable monomer.

2. Description of the Prior Art

Crosslinked polyvinylpyrrolidone (PVP) is made by popcorn or proliferous polymerization of vinylpyrrolidone (VP), in the absence or presence of crosslinking agents, as described in U.S. Pat. Nos. 3,277,066; 3,306,886; 3,759,880; 3,933,766; and 3,992,562; and by F. Haaf et al. in Polymer J. 17. (1), p. 143-152 (1985), in an article entitled, "Polymers of N-Vinylpyrrolidone: Synthesis, Characterization and Uses". Polymerization of vinylpyrrolidone can occur in the absence of added crosslinker because the requisite crosslinker in the process is formed in situ during the first stage heating of vinylpyrrolidone in aqueous caustic solutions at temperatures > 100° C., e.g. at 140° C. These in situ crosslinkers have been identified in the gas phase by gas chromatography and other analytical techniques as 1-vinyl-3-ethylidene pyrrolidone and ethylidene-bis-3-(N-vinylpyrrolidone). These compounds also are believed to be present in very small amounts in reaction mixtures which had been cooled to room temperature. However, after the polymerization was completed, these bifunctional compounds, could not be found in the final polymer product. Accordingly, the named bifunctional monomers have been considered to be present only in small amounts during the polymerization and are consumed in the process of forming the crosslinked PVP polymer.

Accordingly, an object of this invention is to provide a method for making a polymerizable reaction solution containing a high amount, i.e. 5-30% by weight of the isomeric compound 1-vinyl-3(E)-ethylidenepyrrolidone as crosslinker and 50-80% vinylpyrrolidone monomer.

This and other objects and features of the invention will be made apparent from the following description of the invention.

SUMMARY OF THE INVENTION

What is provided herein is a method of making a polymerizable reaction solution containing 50-80% by weight of vinylpyrrolidone monomer, and 5-30% by weight of the isomeric compound 1-vinyl-3(E)-ethylidene pyrrolidone (EVP) having the formula:

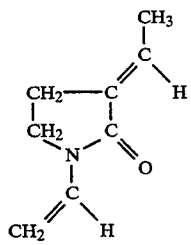

which, in solid form, has a purity of at least 95%, and are white, needle-shaped crystals having a melting point of 59°-61° C.

This isomeric compound exists in the (E) form, which is defined as the isomer in which the methyl group of the ethylidene radical is positioned away from the oxygen atom of the pyrrolidone ring.

The desired polymerizable reaction solution is obtained herein as the organic layer formed by reaction of vinylpyrrolidone in a strongly basic aqueous solution. The reaction is carried out in a 2-phase aqueous-organic system, at an elevated temperature, and under vigorous agitation. The organic layer then is isolated by separating it from the aqueous layer in the reaction product.

DETAILED DESCRIPTION OF THE INVENTION

In accordance with the present invention, the polymerizable reaction solution containing 50-80% vinylpyrrolidone and 5-30% of the isomeric EVP compound is produced in a 2-phase reaction mixture comprising an organic phase which is vinylpyrrolidone (VP) monomer, present in an amount of about 25-90%, preferably 40-75%, and, most preferably, about 60% by weight of the reaction mixture, and an aqueous phase which is a strongly basic solution, such as caustic (NaOH or KOH), or a tetraalkyl ammonium hydroxide solution, suitably with a base concentration of about 2-50%, preferably about 5-10% by weight of the mixture.

The reaction mixture then is heated to a reaction temperature of about 120°-170° C., preferably 130°-140° C., in a closed system, under an inert atmosphere, at ordinary or higher initial pressures, suitably at an initial pressure of 0-3 bars of an inert gas, such as nitrogen. The time required to convert VP monomer in this system to a high concentration of isomeric EVP compound is about 0.5-10 hours, and, preferably 1-3 hours at 140° C., while the reaction mixture is subjected to vigorous agitation.

At the conclusion of the reaction, 2 layers are formed as the reaction product. The top layer is an organic layer which is the desired polymerizable reaction solution containing about 50-80% by weight of unreacted VP and about 5-30% of the isomeric (E) EVP compound. Typically, the solution contains about 70-75% by weight VP and 15-20% by weight EVP. This polymerizable reaction solution can be used for the preparation of crosslinked polyvinylpyrrolidone in the absence of base and at relatively low temperatures, e.g. 100° C. The bottom layer in the reaction product is an aqueous layer which contains small amounts of VP and some EVP.

Upon separation of the organic and aqueous layers, the polymerizable reaction solution is made available for directly carrying out the polymerization reaction to form crosslinked PVP. If desired, water, other comonomers or initiators may be added to the solution to obtain crosslinked polymers which have predetermined chemical and physical properties.

The process of rapid and efficient production of a solution of isomeric (E) EVP in large quantities herein is based on the following interdependent parameters.

(1) An initial high concentration of caustic catalyst in the reaction mixture, and (2) Maintenance of a two-phase organic/aqueous system in the reaction mixture throughout the course of the reaction.

Considering parameter (1), the use of a high (2–50%) caustic concentration has a dual effect. First, the high concentration of a strong inorganic hydroxide causes the aqueous layer to maintain its integrity and "salt out" the organic compounds, most notably, vinylpyrrolidone. Such is not the case in conventional PVP syntheses using a low concentration of caustic solution in which the aqueous and organic phases merge. Secondly, the high caustic concentration in the process of the invention accelerates the reaction of VP to EVP. Indeed, the caustic, which is a catalyst for the formation of EVP from VP, is consumed through reaction with 2-pyrrolidone, a by-product of the reaction. The 2-pyrrolidone, in turn, is readily hydrolyzed by base to sodium 4-aminobutyrate (4-AB), which is not a catalyst for EVP formation. However, (4-AB), being water soluble, can serve as the salt necessary to maintain the 2-phase system in the process.

Transfer of the vinyl moiety of the VP monomer which is necessary for EVP synthesis appears to take place at or near the organic-water interface of the 2-phase reaction system. Once the VP transfer is complete, the slightly acidic 2-pyrrolidone by-product drifts into the basic aqueous phase and EVP moves to the organic medium. In fact, both the strong base and other salts are present overwhelmingly in the aqueous layer during the process. The conversion of 2-pyrrolidone to 4-AB in the presence of aqueous base reduces the concentration of base in the organic phase, thereby avoiding an undesired further reaction of EVP to ethylidene-bis-vinylpyrrolidone (EVBP) and other related organic molecules.

The invention will now be illustrated with reference to the following examples.

EXAMPLE 1

A 1-1 reaction vessel equipped with a reflux condenser and a mechanical stirrer was charged with 100 g of vinylpyrrolidone (VP) monomer and 300 g of B.F. Goodrich Caustic 20 solution (20% NaOH). The 2-phase reaction mixture was given a blanket of nitrogen and heated to 100° C. where it was held for 5 hours while stirring vigorously at 800 rpm. The reaction product consisted of a top organic layer and a bottom aqueous layer. The two layers were separated. 80 g. of the organic layer was collected; it contained 15% by weight of isomeric (E) EVP and 75% by weight of vinylpyrrolidone.

EXAMPLE 2

The procedure of Example 1 was followed using a reaction mixture of 150 g of VP, 180 g of a 50 wt. % NaOH solution and 270 g of distilled water. 120 g. of the organic layer was obtained; it contained 20% by weight of the isomeric (EVP) compound and 70% by weight of vinylpyrrolidone.

EXAMPLES 3–4

A stainless steel Buchi reactor was used as the reaction vessel at an initial pressure of 3 bars of nitrogen pressure and at room temperature. The reaction was carried out at 140° C. for 2 hours using 240 g. of VP, 80 g. of 50% NaOH solution and 80 g. of distilled water (Ex. 3), and 320 g. of VP and 80 g. of 50% NaOH solution (Ex. 4), to provide yields of 25% by weight, and 28% by weight, respectively, of the isomeric compound in the organic layer.

EXAMPLE 5

A reaction mixture of 80% VP and 5% NaOH was heated at 140° C. for 2 hours under 3 bars of $N_2$ pressure (14 ppm $O_2$ only). The organic reaction product (top layer) was separated from the aqueous phase; it was found to contain 75% VP and about 19% of the isomeric (E) compound based on the total mixture of the organic layer.

The isomeric EVP compound in the polymerizable reaction solution of the invention functions as a crosslinking agent in the direct polymerization of vinylpyrrolidone to crosslinked polyvinylpyrrolidone at low temperatures, e.g. 80°–120° C. in the absence of base.

While the invention has been described with particular reference to certain embodiments thereof, it will be understood that changes and modifications may be made which are within the skill of the art. Accordingly, it is intended to be bound only by the following claims, in which:

What is claimed is:

1. A process for obtaining a polymerizable reaction solution as an organic layer containing 5–30% by weight of the isomeric compound 1-vinyl-3(E)-ethylidene pyrrolidone as crosslinker and 50–80% by weight of vinylpyrrolidone monomer which comprises:
   (a) providing a 2-phase reaction mixture comprising an organic phase which is vinylpyrrolidone in an amount of about 25–90% by weight of the mixture, and an aqueous phase which is a solution containing about 2–50 wt. % of a strong base under vigorous agitation, in an inert atmosphere,
   (b) heating said reaction mixture at about 120°–170° C. for about 0.5–10 hours to form a reaction product which includes organic and aqueous layers, and
   (c) separating the organic layer from the aqueous layer.

2. A process according to claim 1 wherein said polymerizable reaction solution contains 15–20% by weight of said isomeric compound and 70–75% by weight of vinylpyrrolidone.

3. A process according to claim 1 wherein the vinylpyrrolidone organic layer is present in an amount of about 40–75% by weight of the mixture and the aqueous phase has 5–10% by weight of base.

4. A process according to claim 1 wherein the reaction temperature is about 130°–140° C.

* * * * *